United States Patent
Li

(10) Patent No.: US 6,187,077 B1
(45) Date of Patent: *Feb. 13, 2001

(54) SEPARATION OF CF$_4$ AND C$_2$F$_6$ FROM A PERFLUOROCOMPOUND MIXTURE

(75) Inventor: Yao-En Li, Buffalo Grove, IL (US)

(73) Assignee: American Air Liquide Inc., Walnut Creek, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/061,977

(22) Filed: Apr. 17, 1998

(51) Int. Cl.$^7$ ............................. B01D 53/22; B01D 53/04
(52) U.S. Cl. ................... 95/47; 95/48; 95/50; 95/131; 95/135
(58) Field of Search .................... 95/45, 47–49, 95/131, 135, 902

(56) References Cited

U.S. PATENT DOCUMENTS

| | | | |
|---|---|---|---|
| 2,947,687 | 8/1960 | Lee | 210/23 |
| 2,953,502 | 9/1960 | Binning et al. | 202/12 |
| 2,960,462 | 11/1960 | Lee et al. | 208/308 |
| 2,970,106 | 1/1961 | Binning et al. | 208/347 |
| 3,508,994 | 4/1970 | Nyrop | 156/280 |
| 3,616,607 | 11/1971 | Klass et al. | 55/16 |
| 3,648,845 | 3/1972 | Riley | 210/490 |
| 3,675,392 * | 7/1972 | Reighter | 95/131 X |
| 4,086,310 | 4/1978 | Bottenbruch et al. | 264/41 |
| 4,113,628 | 9/1978 | Alegranti | 210/500 |
| 4,132,824 | 1/1979 | Kimura et al. | 428/516 |
| 4,155,793 | 5/1979 | Salemme et al. | 156/246 |
| 4,156,597 | 5/1979 | Browall | 55/16 |
| 4,192,824 | 3/1980 | Robinson et al. | 585/409 |
| 4,378,324 | 3/1983 | Makino et al. | 364/41 |
| 4,460,526 | 7/1984 | Makino et al. | 264/41 |
| 4,474,662 | 10/1984 | Makino et al. | 264/41 |
| 4,485,056 | 11/1984 | Makino et al. | 264/41 |
| 4,512,893 | 4/1985 | Makino et al. | 210/500 |
| 4,602,922 | 7/1986 | Cabasso et al. | 55/158 |
| 4,664,669 | 5/1987 | Ohyabu et al. | 623/66 |
| 4,689,267 | 8/1987 | Takamizawa et al. | 428/376 |
| 4,701,187 | 10/1987 | Choe et al. | 55/16 |
| 4,713,292 | 12/1987 | Takemura et al. | 428/373 |
| 4,714,481 | 12/1987 | Matsuura et al. | 55/158 |
| 4,717,394 | 1/1988 | Hayes | 55/158 |
| 4,741,829 | 5/1988 | Takemura et al. | 210/500 |
| 4,756,932 | 7/1988 | Puri | 427/175 |
| 4,826,599 | 5/1989 | Bikson et al. | 210/500 |
| 5,085,676 | 2/1992 | Ekiner et al. | 55/158 |
| 5,332,424 * | 7/1994 | Rao et al. | 95/49 X |
| 5,417,742 * | 5/1995 | Tamhankar et al. | 95/131 X |
| 5,720,797 * | 2/1998 | Yates et al. | 95/135 X |
| 5,730,779 | 3/1998 | Chernyakov et al. | 95/45 |
| 5,759,237 * | 6/1998 | Li et al. | 95/131 X |
| 5,779,763 * | 7/1998 | Pinnau et al. | 95/45 X |
| 5,814,127 * | 9/1998 | Li | 95/131 X |
| 5,843,208 * | 12/1998 | Anumakonda et al. | 95/47 |
| 5,855,647 * | 1/1999 | Li et al. | 95/47 X |
| 5,858,065 * | 1/1999 | Li et al. | 95/47 X |

FOREIGN PATENT DOCUMENTS

| | | |
|---|---|---|
| 63-126522 | 5/1988 | (JP) . |
| 3-284335 | 12/1991 | (JP) . |
| 6-254367 | 9/1994 | (JP) . |

* cited by examiner

Primary Examiner—Robert H. Spitzer
(74) Attorney, Agent, or Firm—Burns, Doane, Swecker & Mathis, L.L.P.

(57) ABSTRACT

A process for separating at least one of CF$_4$ and C$_2$F$_6$ from a gas. The process includes the steps of:

(a) contacting a gas mixture comprising (i) at least one of CF$_4$ and C$_2$F$_6$, (ii) at least one of NF$_3$, CHF$_3$, and N$_2$, and (iii) SF$_6$ with a membrane at conditions effective to obtain a retentate stream rich in SF$_6$ and at least one of CF$_4$ and C$_2$F$_6$, and a permeate stream rich in at least one of NF$_3$, CHF$_3$, and N$_2$; and (b) contacting the retentate stream with an adsorbent at conditions effective to adsorb SF$_6$ and produce a product stream rich in at least one of CF$_4$ and C$_2$F$_6$.

12 Claims, 1 Drawing Sheet

Process Schematic Diagram

Process Schematic Diagram

SEPARATION OF CF$_4$ AND C$_2$F$_6$ FROM A PERFLUOROCOMPOUND MIXTURE

FIELD OF THE INVENTION

The present invention generally relates to a gas separation process. The invention particularly relates to a process for separating CF$_4$ and C$_2$F$_6$ from a perfluorocompound gas mixture by a hybrid system involving membrane and adsorption separation techniques.

BACKGROUND OF THE INVENTION

Various fluorinated hydrocarbon gases including tetrafluoromethane (CF$_4$) and hexafluoroethane (C$_2$F$_6$) are used in the semiconductor industry to etch silica materials for use in integrated circuits. A major use of C$_2$F$_6$, for example, is as a plasma etchant in semiconductor device fabrication. Gases of high purity are critical for this application. It has been found that even small amounts of impurities in the etchant gas can increase the defect rate in the production of these integrated circuits. Thus, there has been a continuous effort in the art to provide a relatively simple and economical process for producing etchant gases having minimal amounts of impurities.

One source of such etchant gases, of course, is the exhaust or vent gas from a semiconductor plasma etching process. The exhaust gas often contains unreacted CF$_4$ and/or C$_2$F$_6$, and other perfluorocompounds (PFCs) such as SF$_6$, NF$_3$, and CHF$_3$ as well as N$_2$. The exhaust gas is usually recovered from the plasma etching process and concentrated from a few parts per million to above 90% by volume in a PFC recovery stage. This concentrated exhaust gas is sometimes referred to as a PFC mixture or a PFC soup. The PFC mixture normally contains about 90% by volume of CF$_4$ and/or C$_2$F$_6$, and about 10% by volume of N$_2$, SF$_6$, NF$_3$, and CHF$_3$.

One way of purifying the PFC mixture to obtain substantially pure CF$_4$ and/or C$_2$F$_6$ is by cryogenic distillation. However, there are some drawbacks to such a process. Cryogenic distillation often requires special equipment and has high utility costs. In addition, the PFC mixture is difficult to separate by cryogenic distillation due to the physical properties of the gaseous components themselves; e.g., CF$_4$ and NF$_3$, and C$_2$F$_6$ and CHF$_3$ form an azeotropic mixture with each other.

It is also known in the art to use activated carbon or zeolites to remove chlorotrifluoromethane (CClF$_3$) and/or fluoroform (CHF$_3$) from C$_2$F$_6$. See, e.g., U.S. Pat. No. 5,523,499. However, this adsorption process is not said to be able to remove N$_2$, SF$_6$, and/or NF$_3$ from a gas mixture such as PFC soup.

Thus, it is an object of the present invention to address this need in the art by providing a process that can separate CF$_4$ and/or C$_2$F$_6$ from a PFC mixture.

This and other objects of the invention will become apparent in light of the following specification, and the appended drawing and claims.

SUMMARY OF THE INVENTION

The present invention relates to a process for separating at least one of CF$_4$ and C$_2$F$_6$ from a gas. The process comprises the steps of:

(a) contacting a gas mixture comprising (i) at least one of CF$_4$ and C$_2$F$_6$, (ii) at least one of NF$_3$, CHF$_3$, and N$_2$, and (iii) SF$_6$ with a membrane at conditions effective to obtain a retentate stream rich in SF$_6$ and at least one of CF$_4$ and C$_2$F$_6$, and a permeate stream rich in at least one of NF$_3$, CHF$_3$, and N$_2$; and (b) contacting the retentate stream with an adsorbent at conditions effective to adsorb SF$_6$ and produce a product stream rich in at least one of CF$_4$ and C$_2$F$_6$.

In a preferred embodiment, the present invention relates to a process for separating both CF$_4$ and C$_2$F$_6$ from a gas. The process comprises the steps of:

(a) contacting a gas mixture comprising CF$_4$, C$_2$F$_6$, NF$_3$, CHF$_3$, N$_2$, and SF$_6$ with a membrane at conditions effective to obtain a retentate stream rich in SF$_6$, CF$_4$, and C$_2$F$_6$, and a permeate stream rich in NF$_3$, CHF$_3$, and N$_2$; and (b) contacting the retentate stream with an adsorbent at conditions effective to adsorb SF$_6$ and produce a product stream rich in CF$_4$ and C$_2$F$_6$.

DETAILED DESCRIPTION OF THE PREFERRED EMBODIMENTS

Figure 1:
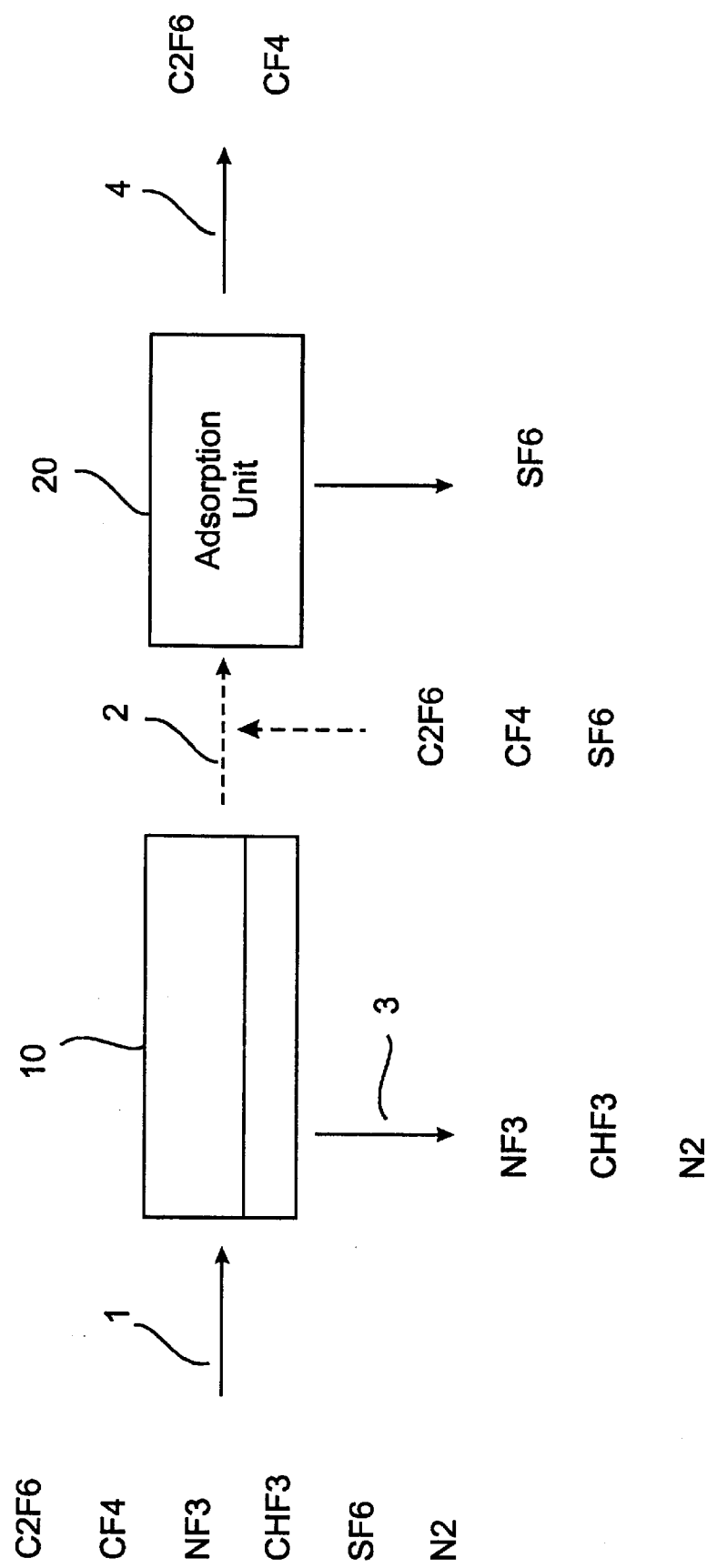
FIG. 1 is a schematic diagram of a process according to the present invention.

The present invention provides a process for separating at least one of CF$_4$ and C$_2$F$_6$ from a gas mixture. The gas mixture preferably comprises (i) at least one of CF$_4$ and C$_2$F$_6$, (ii) at least one of NF$_3$, CHF$_3$, and N$_2$, and (iii) SF$_6$. More preferably, the gas mixture is an exhaust or vent gas from semiconductor fabrication process which comprises CF$_4$, C$_2$F$_6$, NF$_3$, CHF$_3$, N$_2$, and SF$_6$. The exhaust gas preferably has undergone an initial recovery or concentration step.

The gas mixture to be separated preferably comprises from about 10 to about 95% by volume of at least one of CF$_4$ and C$_2$F$_6$. The balance of the gas mixture preferably comprises SF$_6$ and at least one of NF$_3$, CHF$_3$, and N$_2$.

The process according to the present invention comprises the steps of contacting the gas mixture with a membrane at conditions effective to obtain a retentate stream rich in SF$_6$ and at least one of CF$_4$ and C$_2$F$_6$, and a permeate stream rich in at least one of NF$_3$, CHF$_3$, and N$_2$; and contacting the retentate stream with an adsorbent at conditions effective to adsorb SF$_6$ and produce a product stream rich in at least one of CF$_4$ and C$_2$F$_6$.

As used herein, the term "rich" means that the concentration of a particular component in that stream is greater than the concentration of the same component in the feed stream to that process step. Likewise, the term "depleted" means that the concentration of a particular component in that stream is less than the concentration of the same component in the feed stream to that process step.

Any membrane can be used in the process of the present invention so long as the membrane can selectively retain SF$_6$ and at least one of CF$_4$ and C$_2$F$_6$ while passing the other components in the gas mixture through. The membrane should also be substantially non-reactive with the gaseous components to be separated.

Membranes suitable for use in the present invention include glassy membranes such as polymer membranes made preferably from polyimides; polyamides; polyamide-imides; polyesters polycarbonates; polysulfones; polyethersulfone; polyetherketone; alkyl substituted aromatic polyesters; blends of polyethersulfone, aromatic polyimides, aromatic polyamides, polyamides-imides, fluorinated aromatic polyimide, polyamide, and polyamide-imides; glassy polymeric membranes such as those disclosed in U.S. Ser. No. 08/247,125 filed May 20, 1994, the content of which is hereby incorporated by reference; cellulose acetates; and blends thereof, copolymers thereof, substituted polymers (e.g. alkyl, aryl) thereof and the like.

Other membranes suitable for use in the present invention include asymmetric membranes. Asymmetric membranes are prepared by the precipitation of polymer solutions in solvent-miscible nonsolvents. Such membranes are typified by a dense separating layer supported on an anisotropic substrate of a graded porosity and are generally prepared in one step. Examples of such membranes and their methods of manufacture are disclosed in U.S. Pat. Nos. 4,113,628; 4,378,324; 4,460,526; 4,474,662; 4,485,056; 4,512,893; 5,085,676; and 4,717,394; all incorporated herein by reference. The '394 and '676 patents disclose preparation of asymmetric separation membranes from selected polyimides. Particularly preferred membranes are polyimide asymmetric gas separation membranes as disclosed in the '676 patent.

Yet other membranes suitable for use in the present invention include composite gas separation membranes. These membranes typically have a dense separating layer on a preformed microporous substrate. The separating layer and the substrate are usually different in composition. Composite gas separation membranes have evolved to a structure of an ultrathin, dense separating layer supported on an anisotropic, microporous substrate. These composite membrane structures can be prepared by laminating a preformed ultrathin dense separating layer on top of a preformed anisotropic support membrane. Examples of such membranes and their methods of manufacture are disclosed in U.S. Pat. Nos. 4,664,669; 4,689,267; 4,741,829; 2,947,687; 2,953,502; 3,616,607; 4,714,481; 4,602,922; 2,970,106; 2,960,462; 4,713,292; 4,086,310; 4,132,824; 4,192,824; 4,155,793; and 4,156,597; all incorporated herein by reference.

Alternatively, composite gas separation membranes may be prepared by multistep fabrication processes, wherein first an anisotropic, porous substrate is formed, followed by contacting the substrate with a membrane-forming solution. Examples of such methods are described in U.S. Pat. Nos. 4,826,599; 3,648,845; and 3,508,994; all incorporated herein by reference.

U.S. Pat. No. 4,756,932 describes how composite hollow-fiber membranes may also be prepared by co-extrusion of multiple polymer solution layers, followed by precipitation in a solvent-miscible nonsolvent.

The membrane used in the present invention can be post-treated with, or coated by, or co-extruded with, a fluorinated or perfluorinated polymer layer in order to increase its ability to withstand harmful constituents in the gas mixture from which PFCs are to be separate, at low levels or temporary contact with such components.

The temperature of the gas mixture and/or the membrane during the contacting step can vary from about −10° C. to about 100° C. Preferably, the temperature is between about 10° C. and 80° C. More preferably, the temperature ranges from ambient, i.e., from about 20° C. to 25° C., to about 60° C.

It is preferred, according to the present invention, to have a pressure drop across the membrane of less than about 2,000 psig. More preferably, the pressure drop ranges from about 3 to about 200 psig. Even more preferably, the pressure drop is about 20 to about 60 psig.

The requisite pressure drop across the membrane can be provided in one of two ways. First, the feed gas stream can be compressed. Preferred compressors are sealed and oil-free, such as the compressors sold under the tradename POWEREX, available from the Powerex Harrison Company of Ohio. Second and more preferably, the pressure drop across the membrane can be established by lowering the pressure on the permeate side of the membrane. To create the lower pressure on the permeate side, a vacuum pump or any other suction device can be used.

The flowrate of the gas mixture across the membrane can vary from about 0 to about $10^5$ Nm$^3$/h per square meter of membrane available for separation. Preferably, the flowrate is from about $10^{-4}$ to about 10 Nm$^3$/h-m$^2$. More preferably, the flowrate is from about 0.01 to about 0.5 Nm$^3$/h-m$^2$.

The membrane separation step preferably yields a retentate stream comprising from about 60 to about 99% of at least one of $CF_4$ and $C_2F_6$, and from about 0.5 to about 4% of $SF_6$. The retentate stream may also contain trace amounts of $NF_3$ and $CHF_3$. This trace amount of impurities may be removed in a subsequent adsorption unit. The membrane separation step also preferably produces a permeate stream comprising from about 10 to about 60% by volume of at least one of $NF_3$, $CHF_3$, and $N_2$.

The adsorption step in the process of the present invention can be carried out by either pressure swing adsorption (PSA) or thermal swing adsorption (TSA). Both adsorption techniques are well known in the art. This step can be carried out with the adsorbent in a packed bed, moving bed, or fluidized bed.

The adsorption step may be conducted at a pressure ranging from 50 to 1.5 bar, and preferably from 20 to 3 bar. From an economic standpoint, the adsorption pressure is mostly dictated by the membrane retentate stream pressure. The temperature for carrying out this step can vary from 30° to 100° C. The flowrate per unit adsorbent (i.e., space velocity) can vary from 20 min$^{-1}$ to 0.1 min$^{-1}$, and preferably from 10 min$^{-1}$ to 1 min$^{-1}$.

Any adsorbent can be used in the process according to the present invention so long as the adsorbent can selectively adsorb $SF_6$ from a gas stream comprising $CF_4$ and $C_2F_6$. Suitable adsorbents include zeolites, activated carbons, carbon molecular sieves, and polymeric adsorbent resins.

Preferably, the zeolite used in the present invention has a silica to alumina molar ratio of 1:1 to 100:1, and more preferably, of 1:1 to 50:1. Even more preferably, the zeolite is an X-type zeolite. Prior to use, the zeolite should be ion-exchanged with Ca, Na, Li, Li/Zn, Be, Mg, or Fe. Exemplary ion-exchanged, X-type zeolites include NaX zeolite, CaX zeolite, and LiX zeolite.

Various commercially available activated carbons may be used in the present invention including BPL, F-300, F-400, and PCB from Calgon, BAC from Union Carbide, and RB2 from Norit. PCB activated carbon sold by Calgon is preferred.

Similarly, various commercially available polymeric adsorbent resins may used in the present invention. An exemplary polymeric adsorbent resin that is suitable for use in the present invention is DOWREX, which is sold by Dow Chemical Company.

The amount of adsorbent used, of course, varies depending on the amount of impurities to be separated and the desired purity of the product gas. Such a determination is within the scope of one skilled in the art.

Following use, the adsorbent is usually regenerated by desorption of the adsorbed impurities such as $SF_6$. Various methods are known in the art for desorbing impurities adsorbed onto the adsorbent. Generally, desorption can be effected by changing any thermodynamic variable which is effective in removing the adsorbed components. For example, desorption may be carried out using a thermal swing cycle, a pressure swing cycle, or a vacuum cycle; all of which are known in the art. Alternatively, the adsorbed components may be removed by using a stripping gas or liquid. The stripping material may be one of the process feed materials or another material such as $N_2$, He, Ar, or steam.

The conditions for carrying out the regeneration step and the amounts of stripping material, if employed, can be readily determined by one of ordinary skill in the art.

The recovery of $CF_4$ and/or $C_2F_6$ from the gas mixture can be further increased either by increasing the number of separation stages or by incorporating one or more feedback (recycle) loops. Such modifications are within the scope of the present invention.

Furthermore, the process according to the present invention can be employed in combination with a cryogenic distillation column to produce high purity $CF_4$ and/or $C_2F_6$. It can also be installed on-site of a semiconductor fabrication facility with a typical PFC recovery unit. This would reduce the shipping volume for off-site purification.

FIG. 1 is a flow diagram of a preferred process of the present invention. A feed gas stream 1 comprising $CF_4$, $C_2F_6$, $NF_3$, $CHF_3$, $N_2$, and $SF_6$ is introduced into a membrane separation unit 10. The feed gas stream 1 is contacted with a membrane at conditions effective to obtain a retentate stream 2 rich in $SF_6$, $CF_4$, and $C_2F_6$, and a permeate stream 3 rich in $NF_3$, $CHF_3$, and $N_2$. The retentate stream 2 is then passed to an adsorption unit 20 in which $SF_6$ and any remaining $NF_3$ and $CHF_3$ are adsorbed. The adsorption unit 20 produces a product stream 4 rich in $CF_4$ and $C_2F_6$.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A process for separating at least one of $CF_4$ and $C_2F_6$ from a gas, said process comprising the steps of:
   (a) contacting a gas mixture comprising (i) at least one of $CF_4$ and $C_2F_6$, (ii) at least one of $NF_3$, $CHF_3$, and $N_2$, and (iii) $SF_6$ with a membrane at conditions effective to obtain a retentate stream rich in $SF_6$ and at least one of $CF_4$ and $C_2F_6$, and a permeate stream rich in at least one of $NF_3$, $CHF_3$, and $N_2$; and
   (b) contacting said retentate stream with an adsorbent at conditions effective to adsorb $SF_6$ and produce a product stream rich in at least one of $CF_4$ and $C_2F_6$.

2. The process according to claim 1, wherein said gas mixture comprises both $CF_4$ and $C_2F_6$, and said retentate stream and said product stream are rich in both $CF_4$ and $C_2F_6$.

3. The process according to claim 1, wherein said gas mixture comprises $NF_3$, $CHF_3$, and $N_2$, and said permeate stream is rich in $NF_3$, $CHF_3$, and $N_2$.

4. The process according to claim 1, wherein said conditions in step (a) comprise a temperature between about 10 and about 80° C., a pressure drop between about 3 and about 200 psig, and a flowrate rate between about $10^{-4}$ and about 10 $Nm^3/h\text{-}m^2$.

5. The process according to claim 1, wherein said membrane is selected from the group consisting of polyimides, polyamides, polyamide-imides, polyesters, polycarbonates, polysulfones, polyethersulfone, polyetherketone, alkyl substituted aromatic polyesters, and blends of polyethersulfone, aromatic polyimides, aromatic polyamides, polyamides-imides, fluorinated aromatic polyimide, polyamide, and polyamide-imides.

6. The process according to claim 1, wherein said adsorbent is a zeolite, activated carbon, or polymeric adsorbent resin.

7. The process according to claim 1, wherein the temperature of the gas mixture during step (a) is from about 20° C. to 25° C.

8. A process for separating $CF_4$ and $C_2F_6$ from a gas, said process comprising the steps of:
   (a) contacting a gas mixture comprising $CF_4$, $C_2F_6$, $NF_3$, $CHF_3$, $N_2$, and $SF_6$ with a membrane at conditions effective to obtain a retentate stream rich in $SF_6$, $CF_4$, and $C_2F_6$, and a permeate stream rich in $NF_3$, $CHF_3$, and $N_2$; and
   (b) contacting said retentate stream with an adsorbent at conditions effective to adsorb $SF_6$ and produce a product stream rich in $CF_4$ and $C_2F_6$.

9. The process according to claim 8, wherein said conditions of step (a) comprise a temperature between about 10 and about 80° C., a pressure drop between about 3 and about 200 psig, and a flowrate rate between about $10^{-4}$ and about 10 $Nm^3/h\text{-}m^2$.

10. The process according to claim 8, wherein said membrane is selected from the group consisting of polyimides, polyamides, polyamide-imides, polyesters, polycarbonates, polysulfones, polyethersulfone, polyetherketone, alkyl substituted aromatic polyesters, and blends of polyethersulfone, aromatic polyimides, aromatic polyamides, polyamides-imides, fluorinated aromatic polyimide, polyamide, and polyamide-imides.

11. The process according to claim 8, wherein said adsorbent is a zeolite, activated carbon, or polymeric adsorbent resin.

12. The process according to claim 8, wherein the temperature of the gas mixture during step (a) is from about 20° C. to 25° C.

* * * * *